(12) United States Patent
Makino et al.

(10) Patent No.: US 8,343,551 B2
(45) Date of Patent: Jan. 1, 2013

(54) NANOCOMPOSITE PARTICLES

(75) Inventors: Kimiko Makino, Shinjuku-ku (JP);
Hiroshi Terada, Shinjuku-ku (JP);
Takehisa Nakajima, Shinjuku-ku (JP);
Keishiro Tomoda, Shinjuku-ku (JP)

(73) Assignee: Tokyo University of Science Educational Foundation Administrative Organization, Tokyo (JP)

( * ) Notice: Subject to any disclaimer, the term of this patent is extended or adjusted under 35 U.S.C. 154(b) by 986 days.

(21) Appl. No.: 12/282,956

(22) PCT Filed: Mar. 16, 2007

(86) PCT No.: PCT/JP2007/055388
§ 371 (c)(1),
(2), (4) Date: Dec. 16, 2008

(87) PCT Pub. No.: WO2007/111163
PCT Pub. Date: Oct. 4, 2007

(65) Prior Publication Data
US 2009/0169637 A1    Jul. 2, 2009

(30) Foreign Application Priority Data

Mar. 17, 2006  (JP) ................................ 2006-075335
Jan. 22, 2007  (JP) ................................ 2007-011484

(51) Int. Cl.
*A61K 9/16* (2006.01)
*A61K 9/50* (2006.01)
*A61K 31/715* (2006.01)
*A61K 31/765* (2006.01)

(52) U.S. Cl. ....... 424/493; 514/53; 424/78.37; 424/499; 977/906

(58) Field of Classification Search .................. 424/493, 424/78.37, 499; 514/53
See application file for complete search history.

(56) References Cited

U.S. PATENT DOCUMENTS

| 6,956,021 B1 | 10/2005 | Edwards et al. |
| 2006/0002996 A1 | 1/2006 | Edwards et al. |

FOREIGN PATENT DOCUMENTS

| JP | A-05-194196 | 8/1993 |
| JP | A-2002-518432 | 6/2002 |
| JP | A-2002-523360 | 7/2002 |
| JP | A-2004-262810 | 9/2004 |
| JP | A-2005-511629 | 4/2005 |
| JP | A-2005-213170 | 8/2005 |

OTHER PUBLICATIONS

Machine-generated English language translation of JP 2004-262810.*
Machine-generated English language translation of JP 2005-213170.*
P. Ahlin, J. Kristl, A. Kristl and F. Vrecer, "Investigation of polymeric nanoparticles as carriers of enalaprilat for oral administration", International Journal of Pharmaceutics, 2002, 239, 113-120.*
Yvette N. Konan, Robert Gurny and Eric Allémann, "Preparation and characterization of sterile and freeze-dried sub-200 nm nanoparticles", International Journal of Pharmaceutics 233 (2002) 239-252.*
Fanny De Jaeghere, Eric Allémann, Jean-Christophe Leroux, Wim Stevels, Jan Feijen, Eric Doelker and Robert Gurny, "Formulation and Lyoprotection of Poly(Lactic Acid-Co-Ethylene Oxide) Nanoparticles: Influence on Physical Stability and in Vitro Cell Uptake", Pharmaceutical Research, 1999, vol. 16, No. 6, pp. 859-866.*

* cited by examiner

*Primary Examiner* — John Pak
*Assistant Examiner* — Nathan W Schlientz
(74) *Attorney, Agent, or Firm* — Oliff & Berridge, PLC (57) ABSTRACT

Nanocomposite particles having good solubility and redispersibility in water are provided. The nanocomposite particles include a sugar material and nanoparticles containing a drug to be delivered and a biodegradable polymer, the sugar material being disaccharide, and a mass ratio of the nanoparticles to the disaccharide being within the range of from 40:60 to 60:40.

9 Claims, 1 Drawing Sheet

NANOCOMPOSITE PARTICLES

TECHNICAL FIELD

The present invention relates to nanocomposite particles including nanoparticles containing a drug to be delivered, and a sugar material.

RELATED ART

Nanoparticles containing a drug to be delivered have various advantages in a Drug Delivery System (DDS). For example, in the case of administration by injection, nanoparticles have great advantages such as a reduction in adverse side effects by selectively concentrating at the liver, the lung, an inflammatory site, or the like to release the drug. Also, in the case of oral administration, an increase in digestive absorption of a physiologically active substance having low absorbability can be expected. In the case of transdermal administration, it is possible to locally administer a physiologically active substance. Further, in the case of directly administering nanoparticles to the alveoli, the nanoparticles have various advantages such as transferring the drug directly to the blood while avoiding capture by alveolar macrophages.

However, with respect to direct handling of the nanoparticles, there are various problems such as adhesion and coagulation, instability, and scattering. Also, in the case of handling the nanoparticles in a dispersion liquid state, the dispersion liquid has problems related to stability such as the occurrence of reaggregation. Further, it is generally considered that an aerodynamic particle diameter must be within the range of from about 1 to about 5 µm for particles that are pulmonarily administered to reach the alveoli, and there is a problem that nanoparticles having a particle diameter smaller than the above-specified range are discharged by exhalation without being deposited at the alveoli after being taken in by direct inhalation. In order to avoid such problems, various nanocomposite particles obtained by coating nanoparticles with a coating substance and having a particle diameter of microsize have been proposed, but nanocomposite particles capable of fully solving the above problems have not yet been disclosed.

For example, Patent Reference 1 discloses nanocomposite particles containing polystyrene beads or silica colloid beads as nanoparticles and a phospholipid and lactose as coating substances. The geometric particle diameter of such nanocomposite particles increases along with an increase in concentration of nanoparticles, but it is disclosed that the aerodynamic particle diameter is irrelevant to the concentration of nanoparticles. Also, it is disclosed that the nanoparticles can be eluted out when the nanocomposite particles are redissolved in ethanol.

Patent Reference 2 discloses a pronanosphere (nanocomposite particles) obtained by coating a nanosphere liposome containing a drug and a phospholipid by using a sugar material as a nucleus and employing a fluid bed granulation method. It is disclosed that by adding water to the nanocomposite particles it is possible to provide a liposome dispersion liquid in which the liposome has an average particle diameter that is substantially the same as that of the liposome before preparation of the nanocomposite particles.

Further, Patent Reference 3 discloses drug-containing composite particles containing biocompatible nanoparticles formed of a drug and a biocompatible polymer, and a sugar alcohol. The drug-containing composite particles are produced by a spray drying fluid bed granulation method, and are secondary particles formed of primary particles suitably used for pulmonarily administration.

Patent Reference 1: Japanese National Phase Publication No. 2005-511629
Patent Reference 2: Japanese Patent Application Laid-Open (JP-A) No. 05-194196
Patent Reference 3: Japanese Patent Application Laid-Open (JP-A) No. 2004-262810

DISCLOSURE OF THE INVENTION

Problems to be Solved by the Invention

The nanocomposite particles disclosed in Patent Reference 1 have insufficient solubility in water due to the large amount of phospholipid included as the coating substance and cannot be said to have sufficient redispersibility in water. Also, since the nanocomposite particles disclosed in Patent Reference 2 are prepared by the fluid bed granulation method, the particle diameter of the nanocomposite particles that can be produced is limited and, in particular, it is difficult to obtain nanocomposite particles having a flying property. Further, since a nanoparticle dispersion liquid obtained by redispersion in water is a liposome dispersion liquid, stability of the thus-obtained nanoparticle dispersion liquid cannot be said to be sufficient. Since the drug-containing composite particles disclosed in Patent Reference 3 have high moisture absorption due to the inclusion of sugar alcohol, handling properties as a pulmonary inhalation preparation are insufficient. Also, due to production by the spray drying fluid bed granulation method, the contained drug is exposed to a high temperature for a long time, as a result of which the drugs that can be contained are limited.

An object of the invention is to provide nanocomposite particles having good solubility in water and exhibiting good redispersibility when brought into contact with water.

Means for Solving the Problems

According to a first aspect of the invention, there is provided nanocomposite particles comprising a sugar material and nanoparticles including a drug to be delivered and a biodegradable polymer, wherein the sugar material is disaccharide; and a mass ratio of the nanoparticles to the disaccharide is within a range of from 40:60 to 60:40.

In the invention, the mass ratio of the nanoparticles to the disaccharide is more preferably within a range of from 45:55 to 55:45.

In the invention, the biodegradable polymer is preferably a biodegradable polymer comprising at least one selected from the group consisting of polylactic acid, polyglycolic acid, poly(lactic acid-glycolic acid), and polycyanoacrylate.

In the invention, the disaccharide is preferably at least one selected from the group consisting of sucrose, maltose, lactose, trehalose, and cellobiose.

In the invention, it is preferable that the biodegradable polymer is a biodegradable polymer comprising at least one selected from the group consisting of polylactic acid, polyglycolic acid, poly(lactic acid-glycolic acid), and polycyanoacrylate and the disaccharide is at least one selected from the group consisting of sucrose, maltose, lactose, trehalose, and cellobiose, and it is more preferable that the biodegradable polymer is a biodegradable polymer comprising poly(lactic acid-glycolic acid) and the disaccharide is lactose and/or trehalose.

The nanocomposite particles of the invention are preferably obtained by spray drying a solution comprising the nanoparticles and the disaccharide. Further, an inlet temperature of a spray drying machine in the spray drying is preferably within a range of from 60° C. to 100° C., and the inlet temperature of the spray drying machine is particularly preferably within a range of from 60° C. to 90° C.

According to a second aspect of the invention, there is provided a production method for the nanocomposite particles, comprising spray drying a solution containing the nanoparticles and the disaccharide.

In the production method of the invention, an inlet temperature of a spray dying machine in the spray drying is preferably within a range of from 60° C. to 100° C., and the inlet temperature of the spray drying machine is particularly preferably within a range of from 60° C. to 90° C.

Effect of the Invention

According to the invention, it is possible to provide nanocomposite particles having good solubility in water and exhibiting good redispersibility when brought into contact with water.

BRIEF DESCRIPTION OF THE DRAWING

FIG. 1A graph showing an aerodynamic particle diameter distribution of Sample (III-2).

BEST MODE FOR CARRYING OUT THE INVENTION

The invention provides nanocomposite particles including a sugar material and nanoparticles containing a drug to be delivered and a biodegradable polymer, wherein the sugar material is disaccharide, and a mass ratio of the nanoparticles to the disaccharide is within the range of from 40:60 to 60:40.

As used herein, the term "nanoparticles" means fine particles having an average particle diameter of less than 1 μm. It is possible to measure the average particle diameter of nanoparticles by a method known in the art (e.g. by using a commercially available wet particle diameter measurement device). From the view points of absorption to living body and retention control in living body of the nanoparticles, the average particle diameter is preferably within the range of from 50 to 900 nm, more preferably from 250 to 900 nm. The particle diameter of the nanoparticles may be chanced depending on the purpose of usage. Also, since the nanoparticles generally have an average particle diameter of less than 1 μm, it is possible to avoid phagocytosis by alveolar macrophage.

Examples of the drug to be delivered contained in the nanoparticles in the invention include a physiologically active substance and a diagnostic agent. Examples of biological activity of the physiologically active substance include therapeutic, diagnostic, and prophylactic activities. Such drugs to be delivered may be used alone or in combination of two or more.

Examples of the physiologically active substance include an inorganic compound, an organic compound, a polypeptide, a nucleic acid, a polysaccharide, and the like having therapeutic, diagnostic, and/or prophylactic activities. Also, examples of a biological activity of the physiologically active substance include a vascular action, a neurotropic action, a hormone action, an anticoagulant action, an immune regulating action, an anti-inflammatory/analgesic action, an antibacterial action, an antitumor action, an antivirus action, an antigen action, an antibody action, an antisense action, and the like without limitation thereto.

As used herein, the term "polypeptide" means those containing two or more amino acids and having an arbitrary size irrespective of presence/absence of modification after translation, such as glycosylation, phosphorylation, or the like. Examples of the polypeptide include a complete protein such as insulin, calcitonin, immune globulin, an antibody, a cytokine (e.g. lymphokine, monokine, chemokine), an interleukin, an interferon, an erythropoietin, a nuclease, a tumor necrosis factor, a colony stimulation factor, an enzyme (e.g. superoxide dismutase, tissue plasminogen activator agent), a tumor suppressor, a blood protein, a hormone, and a hormone analogue (e.g. growth hormone, adrenocorticotropic hormone, luteinizing hormone-releasing hormone), a vaccine (e.g. tumor antigen, bacterial antigen, virus antigen), an antigen, a blood coagulation factor, a growth factor, and a granulocyte colony simulation factor, a mutein, and active fragments thereof. Examples of physiologically active actions of the polypeptide include a protein inhibitor, a protein antagonist, and a protein agonist without limitation thereto. As used herein, the term "nucleic acid" means a polynucleotide having a DNA sequence or an RNA sequence having an arbitrary length, and examples thereof include a gene (e.g. antisense molecule capable of linking to a complementary DNA for inhibiting transcription, etc.) and ribozyme. Also, polysaccharide such as heparin may be used.

The nanoparticles of the invention may contain a physiologically active substance for the purpose of detecting an analysis object for diagnosis. Examples of the physiologically active substance include an antigen, an antibody (monochlonal or polychlonal), a receptor, hapten, an enzyme, a protein, polypeptide, a nucleic acid (e.g. DNA or RNA), a hormone, and a polymer, and the nanoparticles may contain at least one of the physiologically active substances. Also, the nanoparticles may be labeled in order to facilitate detection of the nanoparticles. Examples of the label include various enzymes, a fluorescent substance, a luminescent substance, a bioluminescent substance, and a radioactive substance without limitation thereto. Appropriate examples of the enzymes include horse radish peroxidase, alkaline phosphatase, β-galactosidase, and acetylcholine esterase. Appropriate examples of the fluorescent substance include umbelliferone, fluorescein, fluorescein isothiocyanate, rhodamine, dichlorotriazinyl amine fluorescein, dansyl chloride, and phycoerythrin. Examples of the luminescent substance include luminol. Examples of the bioluminescent substance include luciferase, luciferin, and aequorin. Appropriate examples of the radioactive substance include $^{125}I$, $^{131}I$, $^{35}S$, and $^{3}H$.

Particularly useful examples of the physiologically active substance include, from the view points of systemic and local therapies, various hormones (e.g. insulin, estradiol, etc.), therapeutic drugs for asthma (e.g. albuterol, etc.), therapeutic drugs for tuberculosis (e.g. rifampicin, ethambutol, streptomycin, isoniazid, pyrazine amide, etc.), therapeutic drugs for cancer (e.g. cisplatin, carboplatin, adriamycin, 5-FU, paclitaxel, etc.), and therapeutic drugs for high blood pressure (e.g. clonidine, prazosin, propranolol, labetalol, bunitrolol, reserpine, nifedipine, furosemide, etc.) without limitation thereto.

The nanoparticles may contain an arbitrary diagnostic agent. It is possible to locally or systemically deliver the diagnostic agent by administering such nanocomposite particles to a patient. Specific examples of the diagnostic agent include a contrast agent without limitation thereto. Examples of the contrast agent include commercially available drugs used in positron emission tomography (PET), computed tomography (CT), single photon emission computed tomography, X-ray, X-ray fluoroscopy, and magnetic resonance imaging (MRI). The diagnostic agent may be detected by employing the standard technology available in the art and a commercially available apparatus.

From the view points of stability of the nanoparticles and stability of the drug to be delivered, the nanoparticles may contain a drug in an amount of 1 to 50 mass %, preferably 5 to 20 mass %, of a mass of the nanoparticles. It is possible to change the content of the drug depending on a desired effect and a release rate or a release period of the drug to be delivered.

The nanoparticles in the invention contain a biodegradable polymer. In general, the biodegradable polymer is degraded to a substance harmless to living body by enzymatic degradation or exposure to water in vivo. Examples of the biodegradable polymer include a polyester compound, a polyamide compound, a polycarbonate compound, a polyvinyl compound, and polysaccharide without limitation thereto. These biodegradable polymers may be used alone or in combination of two or more.

Specific examples of the polyester compound include polylactic acid, polyglycolic acid, polycaprolactone, and copolymers thereof, as well as polybutylene succinate, polyethylene succinate, poly(butylene succinate/adipate), poly(butylene succinate/carbonate), poly(butylene succinate/telephthalate), poly(butylene adipate/telephthalate), poly(tetramethylene adipate/telephthalate), and poly(butylene succinate/adipate/telephthalate) without limitation thereto.

Specific examples of the polyamide compound include polyleucine, specific examples of the polyvinyl compound include polycyanoacrylate, and specific examples of the polysaccharide include cellulose without limitation thereto.

Among these biodegradable polymers, it is preferable to use at least one selected from polylactic acid, polyglycolic acid, poly(lactic acid-glycolic acid) (PLGA), and polycyanoacrylate, and it is more preferable to use PLGA.

By appropriately selecting a type and a molecular weight of the biodegradable polymer, it is possible to control a release rate of the drug from the nanoparticles and a biodegradation rate. For example, in the case where the biodegradable polymer is PLGA, the molecular weight is preferably 1500 to 150000, more preferably 1500 to 75000. It is possible to provide the nanoparticles capable of easily releasing a biodegradable substance. Also, in the case where the biodegradable polymer is a copolymer, it is possible to control the release rate of the drug from nanoparticles and the biodegradation rate by appropriately selecting a composition ratio of each of monomers.

Further, the nanoparticles may be modified so as to control the release rate of the drug from nanoparticles and the biodegradation rate.

The nanoparticles may contain various additives as required. Specific examples of the additives include a surfactant, a water soluble polymer, and a lipid without limitation thereto. It is possible to further enhance the redispersibility of the nanoparticles by adding such additives. Specific examples of the water soluble polymer include polyvinyl alcohol, polyethylene glycol, polyethylene oxide, and the like, and specific examples of the lipid include phospholipid, cholesterol, and the like. These additives may be used alone or in combination of two or more.

It is possible to prepare the nanoparticles in the invention by a method known in the art, such as dry milling, wet milling, emulsion polymerization, interfacial polymerization, spray drying, thermofusion microencapsulation, emulsion solvent diffusion, and the like without limitation thereto. Particularly, from the view point of easy particle diameter control, the emulsion solvent diffusion method employing supersonic emulsification may preferably be employed.

The nanocomposite particles of the invention contain the nanoparticles and the disaccharide, and a large part thereof has a structure wherein the nanoparticles and the disaccharide form a network. Since the nanocomposite particles contain the disaccharide, it is possible to obtain the nanocomposite particles that are excellent in redispersibility of nanoparticles and handling property.

The disaccharide is not particularly limited insofar as the disaccharide is obtained by bonding of two molecules of monosaccharide (e.g. glucose, fructose, galactose, etc.). A combination of the monosaccharide is not particularly limited, but, from the view points of redispersibility of the nanoparticles and handling property, any one of two molecules of glucose, glucose and fructose, galactose and glucose is preferred. Also, a mode of glycoside bonding is not limited, and the bonding may be any one of an α1,4 bonding, a β1,4 bonding, and a 1,1 bonding. Specific examples of the disaccharide include sucrose, maltose, lactose, trehalose, cellobiose, and the like.

In the invention, it is preferable to use at least one selected from sucrose, maltose, lactose, trehalose, and cellobiose among the above-listed disaccharide from the view points of water solubility of disaccharide, redispersibility of nanoparticles, and handling property of nanocomposite particles, and it is more preferable to use at least one selected from trehalose and lactose. These disaccharides may be used alone or in combination of two or more.

A mass ratio of the nanoparticles to the disaccharide in the nanocomposite particles of the invention is within the range of from 40:60 to 60:40 from the view point of redispersibility of the nanoparticles. There is a tendency of incomplete redispersion of nanocomposite particles when the mass ratio is outside the range. That is, although the nanocomposite particles partly release the nanoparticles contained therein, the rest causes coagulation or insolubilization so that a particle diameter distribution of the redispersion liquid has a polydisperse system. Further, it is possible to achieve a better particle diameter distribution by maintaining the mass ratio within the more preferable range of from 45:55 to 55:45.

The nanocomposite particles of the invention may contain various additives as required. Examples of the additives include a buffer salt, a fatty acid, a fatty acid ester, a phospholipid, an inorganic compound, a phosphate, and the like.

It is possible to prepare the nanocomposite particles of the invention by a method known in the art. For example, it is possible to employ a spray drying method, a membrane emulsification method, freeze drying, a tumbling granulation method, a fluid bed granulation method, and the like without limitation thereto. Particularly, it is preferable to perform the preparation by employing the spray drying method from the view points of capability of easy particle diameter control and the short particle drying time.

One of ordinarily employed spray drying techniques is disclosed in Spray Drying Handbook, K. Masters, John Wiley & Sons, New York, 1984. In general, in the spray drying, a heat derived from a heated gas such as a heated air or heated nitrogen is used for evaporating a solvent from droplets formed by an spraying device under a temperature gradient between an inlet temperature immediately after spraying and an outlet temperature at termination of drying, thereby obtaining spray dried particles.

For the spraying device, an spraying technology known in the art may be employed. For example, a liquid pressure press nozzle spraying device, a two-stream spraying device, a supersonic spraying device, a centrifugal spraying device including a rotating plate or a wheel are usable without limitation thereto.

It is possible to prepare the nanocomposite particles of the invention by using a commercially available spray drying machine, for example. An inlet temperature in a drying zone immediately after spraying may appropriately be selected depending on the spray drying machine to be used, the composition of the nanoparticle dispersion liquid to be spray dried, and the like and may preferably be within the range of from 60° C. to 100° C., more preferably within the range of from 60° C. to 90° C. In the case where the inlet temperature is low, a reduction in productivity and an increase in average particle diameter tends to occur due to insufficient drying rate. Also, in the case where the inlet temperature is too high, good redispersibility is not achieved in some cases. It is possible to assume that such case is attributable to alteration of disaccharide by the high temperature.

Particularly, in the case of using the nanocomposite particles as a pulmonary administration preparation, the inlet temperature may preferably be 70° C. to 120° C., more preferably 80° C. to 120° C., in order to obtain nanocomposite particles having an aerodynamic particle diameter.

It is possible to measure or calculate the aerodynamic particle diameter by a method known in the art. For example, it is possible to perform the measurement by using a cascade impactor employing aerodynamic classification mechanism. Also, the aerodynamic particle diameter ($d_{aer}$) is calculated from the following expression (1) using a geometric particle diameter ($d_s$) and a density ($\rho$).

$$d_{aer} = d_s \times \text{square root of } \rho \quad (1).$$

The cascade impactor is used for evaluating the aerodynamic particle diameter distribution of pulmonary absorption preparations, and it is possible to perform the evaluation in accordance with US pharmacopeia. For instance, the method using an Andersen type cascade impactor is a method for evaluating the aerodynamic particle diameter distribution by measuring to which stage among stages 0 to 7 a fine powder charged from an upper part of the device reaches while sucking with a pump. The upper the stage, the larger the sieve opening, and the lower the stage, the smaller the sieve opening. Therefore, the particles deposited on the upper stage have a larger aerodynamic particle diameter. More specifically, particles having an aerodynamic particle diameter larger than 4.7 μm are deposited on the stages 0 to 2, and particles having an aerodynamic particle diameter of from 0.13 to 4.7 μm are deposited on the stages 3 to 7. It is possible to evaluate the aerodynamic particle diameter by measuring a mass of particles deposited in each of the stages.

Water or a buffer solution is used as a solvent for preparing a sugar solution in which the nanoparticles to be used for the spray drying are dispersed. An organic solvent may also be contained. Appropriate examples of the organic solvent include an alcohol (e.g. methanol, ethanol, propanol, isopropyl alcohol, butanol, etc.), perfluorocarbon, dichloromethane, chloroform, ether, ethyl acetate, methyl-tert-butylether, acetone, and the like without limitation thereto.

The nanocomposite particles of the invention are useful as a pulmonary absorption preparation in the case where the nanocomposite particles are prepared so as to have an aerodynamic particle diameter appropriate for delivery to the alveoli. Also, since the nanocomposite particles of the invention have high water solubility, they are useful for an injection preparation, an oral absorption preparation, a transmucosal absorption preparation, a transdermal absorption preparation, and an ophthalmic preparation due.

Hereinafter, specific examples of the invention will be described to describe the invention in more details. However, the invention is not limited to the examples.

Example 1

(1) Preparation of Nanoparticles

In 10 mL of dichloromethane, 0.05 g of rifampicin and 0.45 g of PLGA (lactic acid:glycolic acid=75:25, molecular weight: 10000) were dissolved, and the mixture was added to 100 mL of a polyvinyl alcohol (manufactured by Wako Pure Chemical Industries, polymerization degree: about 500) aqueous solution. By using a supersonic wave generator (S-250D manufactured by BRANSON), irradiation with a supersonic wave at an output of 110 W was performed for 20 seconds. The thus-obtained O/W emulsion was stirred for 3 hours at a room temperature to evaporate dichloromethane. The thus-obtained S/W dispersion liquid was subjected to centrifugation at 10000 rpm for 10 minutes, followed by collection of precipitated rifampicin-containing PLGA nanoparticles. Distilled water was added to the nanoparticles to perform redispersion, and centrifugation at 10000 rpm was performed for 10 minutes again, followed by collection of precipitated nanoparticles. This operation was repeated for three times.

The thus-obtained nanoparticles were dispersed in distilled water, and a particle diameter distribution was measured by using a wet particle diameter measurement device (ZETA SIZER HSA3000 manufactured by MALVERN). The thus-obtained nanoparticles exhibited a particle diameter distribution of a single dispersion. An average particle diameter thereof was about 500 nm.

(2) Preparation of Nanocomposite Particles

The PLGA nanoparticles obtained by the above-described nanoparticle preparation method were redispersed in 100 mL of a distilled water by varying a mass thereof as shown in Table 1 to Table 6, and trehalose was added to and dissolved in each of the dispersion liquids by varying a mass thereof as shown in Table 1 to Table 6. Each of the trehalose solutions in which the nanoparticles were dispersed was supplied to a spray drying machine (Minispray Dryer B290 Type manufactured by BUCHI) to prepare nanocomposite particles. Conditions for the spray drying were a spray gun diameter of 0.75 mm, an inlet temperature of 90° C., a drying air amount of 22 m³/hr, a spraying air amount of 536 L/hr, and a sample supply rate of 1.2 mL/min.

(3) Measurement of Dry Average Particle Diameter Distribution of Nanocomposite Particles A particle diameter distribution in the air of the nanocomposite particles obtained as described above was measured by using a dry particle diameter measurement device (LDSA-3500A manufactured by Tonichi Computer Applications Co., Ltd.) to calculate a dry average particle diameter ($d_s$)(μm).

(4) Measurement of Specific Gravity of Nanocomposite Particles and Calculation of Aerodynamic Particle Diameter A specific gravity of the nanocomposite particles obtained as describe above was measured by using a particle specific gravity meter (ULTRAPYCOMETER1000 manufactured by Quantachrome Inc.). An aerodynamic particle diameter ($d_{aer}$) (μm) of the particles was calculated by the following expression (1) by using the dry particle diameter ($d_s$)(μm) and a particle density ($\rho$).

$$d_{aer} = d_s \times \text{square root of } \rho \quad (1).$$

(5) Measurement of Wet Particle Diameter Distribution of Nanocomposite Particles Next, 0.005 g of the nanocomposite particles were redispersed in 10 mL of distilled water, and a wet particle diameter distribution thereof was measured by using a wet particle diameter measurement device (ZETA SIZER HSA3000 manufactured by MALVERN). The measurement was performed immediately after the redispersion and also at 10 minutes after the redispersion as required.

The masses of the nanoparticles and trehalose, the measurement results of the dry average particle diameters, and the measurement results of the wet particle diameter distributions of the obtained nanocomposite particles are shown in Table 1 to Table 6.

TABLE 1

| Sample No. | I-1 | Sample No. | I-2 |
|---|---|---|---|
| Nanoparticles (g) | 0.2 | Nanoparticles (g) | 0.4 |
| Trehalose (g) | 1.8 | Trehalose (g) | 1.6 |
| Dry Average Particle Diameter (μm) | 2.12 | Dry Average Particle Diameter (μm) | 2.47 |
| Specific Gravity | 1.49 | Specific Gravity | 1.44 |
| Aerodynamic Particle Diameter (μm) | 2.59 | Aerodynamic Particle Diameter (μm) | 2.97 |

| Wet Particle Diameter Distribution (immediately after) | | Wet Particle Diameter Distribution (10 minutes after) | | Wet Particle Diameter Distribution (immediately after) | | Wet Particle Diameter Distribution (10 minutes after) | |
|---|---|---|---|---|---|---|---|
| Particle Diameter (nm) | Volume (%) | Particle Diameter (nm) | Volume (%) | Particle Diameter (nm) | Volume (%) | Particle Diameter (nm) | Volume (%) |
| 33 | 0.0 | 36 | 0.0 | 15 | 0.0 | 24 | 0.0 |
| 44 | 0.0 | 47 | 0.0 | 21 | 0.0 | 31 | 0.0 |
| 59 | 0.0 | 62 | 0.0 | 29 | 0.0 | 42 | 0.0 |
| 78 | 0.0 | 82 | 0.0 | 41 | 0.0 | 55 | 0.0 |
| 104 | 0.0 | 108 | 0.0 | 57 | 0.0 | 73 | 0.0 |
| 139 | 0.0 | 142 | 0.0 | 80 | 0.0 | 97 | 0.0 |
| 185 | 0.0 | 187 | 0.0 | 111 | 0.0 | 129 | 0.0 |
| 247 | 0.0 | 247 | 0.1 | 156 | 0.0 | 171 | 0.0 |
| 329 | 0.8 | 325 | 4.6 | 217 | 0.0 | 227 | 0.1 |
| 439 | 1.6 | 429 | 9.4 | 304 | 6.0 | 301 | 7.1 |
| 585 | 1.3 | 565 | 13.1 | 425 | 12.4 | 400 | 16.2 |
| 779 | 1.9 | 745 | 19.0 | 594 | 6.9 | 531 | 17.0 |
| 1038 | 2.9 | 981 | 18.4 | 831 | 0.5 | 704 | 13.2 |
| 1384 | 2.0 | 1293 | 13.9 | 1161 | 0.0 | 935 | 5.4 |
| 1844 | 1.0 | 1704 | 11.1 | 1623 | 0.0 | 1241 | 0.0 |
| 2458 | 0.6 | 2245 | 7.6 | 2269 | 0.0 | 1647 | 0.0 |
| 3277 | 0.2 | 2959 | 2.8 | 3172 | 0.0 | 2186 | 6.6 |
| 4367 | 0.2 | 3899 | 0.0 | 4434 | 3.4 | 2901 | 16.8 |
| 5820 | 0.7 | 5139 | 0.0 | 6199 | 22.0 | 3850 | 13.9 |
| 7758 | 2.5 | 6771 | 0.0 | 8666 | 33.8 | 5110 | 3.7 |
| 10339 | 23.4 | 8923 | 0.0 | 12115 | 15.2 | 6781 | 0.0 |
| 13781 | 41.1 | 11759 | 0.0 | 16937 | 0.0 | 9000 | 0.0 |
| 18367 | 19.7 | 15496 | 0.0 | 23677 | 0.5 | 11945 | 0.0 |
| 24480 | 0.0 | 20420 | 0.0 | 33100 | 0.0 | 15854 | 0.0 |
| Average Particle Diameter (nm) | 12074.6 | Average Particle Diameter (nm) | 1073.9 | Average Particle Diameter (nm) | 6519.6 | Average Particle Diameter (nm) | 1675.8 |
| Remarks | | Comparative Example | | Remarks | | Comparative Example | |

TABLE 2

| Sample No. | I-3 | Sample No. | I-4 |
|---|---|---|---|
| Nanoparticles (g) | 0.6 | Nanoparticles (g) | 0.8 |
| Trehalose (g) | 1.4 | Trehalose (g) | 1.2 |
| Dry Average Particle Diameter (μm) | 2.07 | Dry Average Particle Diameter (μm) | 1.77 |
| Specific Gravity | 1.43 | Specific Gravity | 1.44 |
| Aerodynamic Particle Diameter (μm) | 2.48 | Aerodynamic Particle Diameter (μm) | 2.12 |

| Wet Particle Diameter Distribution (immediately after) | | Wet Particle Diameter Distribution (10 minutes after) | | Wet Particle Diameter Distribution (immediately after) | | Wet Particle Diameter Distribution (10 minutes after) | |
|---|---|---|---|---|---|---|---|
| Particle Diameter (nm) | Volume (%) | Particle Diameter (nm) | Volume (%) | Particle Diameter (nm) | Volume (%) | Particle Diameter (nm) | Volume (%) |
| 7 | 0.0 | 21 | 0.0 | 70 | 0.0 | 14 | 0.0 |
| 11 | 0.0 | 28 | 0.0 | 82 | 0.0 | 19 | 0.0 |
| 16 | 0.0 | 37 | 0.0 | 97 | 0.0 | 26 | 0.0 |

TABLE 2-continued

| Particle Diameter (nm) | Volume (%) | Particle Diameter (nm) | Volume (%) | Particle Diameter (nm) | Volume (%) | Particle Diameter (nm) | Volume (%) |
|---|---|---|---|---|---|---|---|
| 23 | 0.0 | 49 | 0.0 | 114 | 0.0 | 35 | 0.0 |
| 34 | 0.0 | 65 | 0.0 | 134 | 0.0 | 48 | 0.0 |
| 50 | 0.0 | 86 | 0.0 | 157 | 0.0 | 66 | 0.0 |
| 73 | 0.0 | 115 | 0.0 | 185 | 0.0 | 91 | 0.0 |
| 107 | 0.0 | 153 | 0.0 | 217 | 0.0 | 125 | 0.2 |
| 157 | 0.1 | 203 | 0.3 | 255 | 0.0 | 172 | 0.7 |
| 230 | 1.1 | 270 | 3.9 | 300 | 1.4 | 237 | 1.7 |
| 337 | 4.7 | 358 | 15.9 | 353 | 22.7 | 326 | 19.6 |
| 495 | 9.4 | 477 | 22.2 | 415 | 44.9 | 448 | 38.1 |
| 726 | 8.7 | 633 | 10.9 | 488 | 27.3 | 616 | 24.5 |
| 1066 | 2.9 | 842 | 1.0 | 574 | 3.7 | 847 | 8.5 |
| 1563 | 0.0 | 1120 | 3.0 | 675 | 0.0 | 1165 | 5.2 |
| 2294 | 0.0 | 1488 | 14.5 | 794 | 0.0 | 1602 | 1.4 |
| 3365 | 0.0 | 1979 | 19.8 | 934 | 0.0 | 2202 | 0.0 |
| 4938 | 0.0 | 2631 | 8.4 | 1098 | 0.0 | 3028 | 0.0 |
| 7245 | 18.3 | 3497 | 0.0 | 1291 | 0.0 | 4164 | 0.0 |
| 10629 | 36.6 | 4649 | 0.0 | 1518 | 0.0 | 5725 | 0.0 |
| 15596 | 18.3 | 6181 | 0.0 | 1785 | 0.0 | 7871 | 0.0 |
| 22882 | 0.0 | 8218 | 0.0 | 2099 | 0.0 | 10823 | 0.0 |
| 33574 | 0.0 | 10925 | 0.0 | 2468 | 0.0 | 14881 | 0.0 |
| 49260 | 0.0 | 14524 | 0.0 | 2902 | 0.0 | 20460 | 0.0 |
| Average Particle Diameter (nm) | 8229.3 | Average Particle Diameter (nm) | 1113.5 | Average Particle Diameter (nm) | 425.4 | Average Particle Diameter (nm) | 546.2 |
| Remarks | Comparative Example | | | Remarks | Example | | |

TABLE 3

| Sample No. | I-5 | Sample No. | I-6 |
|---|---|---|---|
| Nanoparticles (g) | 0.9 | Nanoparticles (g) | 1.0 |
| Trehalose (g) | 1.1 | Trehalose (g) | 1.0 |
| Dry Average Particle Diameter (μm) | 1.77 | Dry Average Particle Diameter (μm) | 1.86 |
| Specific Gravity | 1.33 | Specific Gravity | 1.31 |
| Aerodynamic Particle Diameter (μm) | 2.04 | Aerodynamic Particle Diameter (μm) | 2.13 |

| Wet Particle Diameter Distribution (immediately after) | | Wet Particle Diameter Distribution (10 minutes after) | | Wet Particle Diameter Distribution (immediately after) | | Wet Particle Diameter Distribution (10 minutes after) | |
|---|---|---|---|---|---|---|---|
| Particle Diameter (nm) | Volume (%) | Particle Diameter (nm) | Volume (%) | Particle Diameter (nm) | Volume (%) | Particle Diameter (nm) | Volume (%) |
| 66 | 0.0 | 36 | 0.0 | 111 | 0.0 | 107 | 0.0 |
| 79 | 0.0 | 45 | 0.0 | 125 | 0.0 | 121 | 0.0 |
| 94 | 0.0 | 57 | 0.0 | 140 | 0.0 | 137 | 0.0 |
| 113 | 0.0 | 72 | 0.0 | 158 | 0.0 | 155 | 0.0 |
| 135 | 0.0 | 90 | 0.0 | 178 | 0.0 | 175 | 0.0 |
| 161 | 0.0 | 113 | 0.0 | 200 | 0.0 | 198 | 0.0 |
| 193 | 0.0 | 143 | 0.0 | 225 | 0.0 | 224 | 0.0 |
| 231 | 0.0 | 180 | 0.0 | 253 | 0.3 | 254 | 0.0 |
| 276 | 0.0 | 226 | 0.2 | 285 | 1.4 | 287 | 0.2 |
| 331 | 8.4 | 285 | 1.9 | 320 | 4.4 | 325 | 2.4 |
| 396 | 31.1 | 358 | 19.2 | 361 | 16.1 | 368 | 21.1 |
| 474 | 39.3 | 451 | 35.0 | 406 | 33.3 | 417 | 41.3 |
| 567 | 18.9 | 568 | 24.8 | 457 | 31.2 | 472 | 28.1 |
| 678 | 2.3 | 715 | 13.0 | 514 | 11.9 | 535 | 6.3 |
| 811 | 0.0 | 900 | 5.7 | 578 | 1.2 | 605 | 0.5 |
| 971 | 0.0 | 1133 | 0.0 | 650 | 0.1 | 685 | 0.0 |
| 1161 | 0.0 | 1427 | 0.0 | 732 | 0.0 | 776 | 0.0 |
| 1390 | 0.0 | 1796 | 0.0 | 824 | 0.0 | 878 | 0.0 |
| 1663 | 0.0 | 2261 | 0.0 | 927 | 0.0 | 994 | 0.0 |
| 1989 | 0.0 | 2846 | 0.0 | 1043 | 0.0 | 1126 | 0.0 |
| 2381 | 0.0 | 3583 | 0.0 | 1173 | 0.0 | 1275 | 0.0 |
| 2848 | 0.0 | 4511 | 0.0 | 1320 | 0.0 | 1443 | 0.0 |
| 3408 | 0.0 | 5678 | 0.0 | 1486 | 0.0 | 1634 | 0.0 |
| 4078 | 0.0 | 7148 | 0.0 | 1672 | 0.0 | 1649 | 0.0 |
| Average Particle Diameter (nm) | 459.6 | Average Particle Diameter (nm) | 517.8 | Average Particle Diameter (nm) | 423.1 | Average Particle Diameter (nm) | 427.8 |
| Remarks | Example | | | Remarks | Example | | |

TABLE 4

| Sample No. | I-7 | Sample No. | I-8 |
|---|---|---|---|
| Nanoparticles (g) | 1.1 | Nanoparticles (g) | 1.2 |
| Trehalose (g) | 0.9 | Trehalose (g) | 0.8 |
| Dry Average Particle Diameter ($\mu$m) | 1.58 | Dry Average Particle Diameter ($\mu$m) | 1.99 |
| Specific Gravity | 1.45 | Specific Gravity | 1.39 |
| Aerodynamic Particle Diameter ($\mu$m) | 1.90 | Aerodynamic Particle Diameter ($\mu$m) | 2.35 |

| Wet Particle Diameter Distribution (immediately after) | | Wet Particle Diameter Distribution (10 minutes after) | | Wet Particle Diameter Distribution (immediately after) | | Wet Particle Diameter Distribution (10 minutes after) | |
|---|---|---|---|---|---|---|---|
| Particle Diameter (nm) | Volume (%) | Particle Diameter (nm) | Volume (%) | Particle Diameter (nm) | Volume (%) | Particle Diameter (nm) | Volume (%) |
| 82 | 0.0 | 42 | 0.0 | 303 | 0.0 | 21 | 0.0 |
| 96 | 0.0 | 52 | 0.0 | 321 | 0.0 | 28 | 0.0 |
| 113 | 0.0 | 65 | 0.0 | 341 | 0.0 | 38 | 0.0 |
| 133 | 0.0 | 80 | 0.0 | 361 | 0.0 | 50 | 0.0 |
| 156 | 0.0 | 99 | 0.0 | 383 | 0.0 | 66 | 0.0 |
| 184 | 0.0 | 123 | 0.1 | 406 | 0.0 | 88 | 0.0 |
| 216 | 0.0 | 152 | 0.1 | 430 | 4.8 | 117 | 0.0 |
| 254 | 0.1 | 189 | 0.1 | 456 | 15.2 | 155 | 0.2 |
| 298 | 1.2 | 234 | 0.3 | 483 | 20.7 | 205 | 0.9 |
| 351 | 13.8 | 290 | 1.7 | 512 | 19.4 | 272 | 4.4 |
| 412 | 29.9 | 359 | 19.0 | 543 | 16.2 | 361 | 17.1 |
| 485 | 24.1 | 445 | 35.7 | 576 | 12.4 | 478 | 28.8 |
| 570 | 12.3 | 552 | 24.2 | 610 | 7.7 | 634 | 24.2 |
| 670 | 10.2 | 684 | 11.6 | 647 | 3.0 | 841 | 14.8 |
| 788 | 6.7 | 848 | 6.3 | 686 | 0.5 | 1116 | 7.8 |
| 927 | 1.7 | 1051 | 0.9 | 727 | 0.0 | 1480 | 2.1 |
| 1090 | 0.0 | 1303 | 0.0 | 770 | 0.0 | 1962 | 0.0 |
| 1281 | 0.0 | 1615 | 0.0 | 817 | 0.0 | 2602 | 0.0 |
| 1507 | 0.0 | 2002 | 0.0 | 866 | 0.0 | 3451 | 0.0 |
| 1772 | 0.0 | 2482 | 0.0 | 918 | 0.0 | 4577 | 0.0 |
| 2083 | 0.0 | 3076 | 0.0 | 973 | 0.0 | 6070 | 0.0 |
| 2449 | 0.0 | 3813 | 0.0 | 1031 | 0.0 | 8049 | 0.0 |
| 2880 | 0.0 | 4726 | 0.0 | 1093 | 0.0 | 10674 | 0.0 |
| 3386 | 0.0 | 5858 | 0.0 | 1158 | 0.0 | 14156 | 0.0 |
| Average Particle Diameter (nm) | 499.5 | Average Particle Diameter (nm) | 509.2 | Average Particle Diameter (nm) | 518.5 | Average Particle Diameter (nm) | 608.1 |
| Remarks | | Example | | Remarks | | Example | |

TABLE 5

| Sample No. | I-9 | Sample No. | I-10 |
|---|---|---|---|
| Nanoparticles (g) | 1.4 | Nanoparticles (g) | 1.6 |
| Trehalose (g) | 0.6 | Trehalose (g) | 0.4 |
| Dry Average Particle Diameter ($\mu$m) | 2.52 | Dry Average Particle Diameter ($\mu$m) | 1.91 |
| Specific Gravity | 1.38 | Specific Gravity | 1.35 |
| Aerodynamic Particle Diameter ($\mu$m) | 2.96 | Aerodynamic Particle Diameter ($\mu$m) | 2.22 |

| Wet Particle Diameter Distribution (immediately after) | | Wet Particle Diameter Distribution (10 minutes after) | | Wet Particle Diameter Distribution (immediately after) | | Wet Particle Diameter Distribution (10 minutes after) | |
|---|---|---|---|---|---|---|---|
| Particle Diameter (nm) | Volume (%) | Particle Diameter (nm) | Volume (%) | Particle Diameter (nm) | Volume (%) | Particle Diameter (nm) | Volume (%) |
| 23 | 0.0 | 24 | 0.0 | 1 | 0.0 | 17 | 0.0 |
| 31 | 0.0 | 32 | 0.0 | 2 | 0.0 | 23 | 0.0 |
| 42 | 0.0 | 43 | 0.0 | 4 | 0.0 | 32 | 0.0 |
| 57 | 0.0 | 58 | 0.0 | 7 | 0.0 | 44 | 0.0 |
| 76 | 0.0 | 77 | 0.0 | 11 | 0.0 | 61 | 0.0 |
| 102 | 0.0 | 104 | 0.0 | 20 | 0.0 | 84 | 0.0 |
| 138 | 0.0 | 139 | 0.0 | 34 | 0.0 | 115 | 0.0 |
| 185 | 0.0 | 186 | 0.0 | 59 | 0.0 | 158 | 0.2 |
| 248 | 0.4 | 249 | 0.4 | 102 | 0.0 | 217 | 0.5 |
| 334 | 12.8 | 333 | 12.9 | 177 | 0.5 | 299 | 6.9 |
| 448 | 25.7 | 446 | 26.1 | 307 | 10.7 | 411 | 13.9 |
| 602 | 15.7 | 597 | 16.7 | 532 | 34.7 | 565 | 14.3 |
| 809 | 4.4 | 799 | 6.0 | 923 | 39.3 | 776 | 19.6 |

TABLE 5-continued

| 1087 | 4.1 | 1070 | 4.4 | 1599 | 14.8 | 1068 | 21.6 |
|---|---|---|---|---|---|---|---|
| 1460 | 11.5 | 1432 | 8.5 | 2772 | 0.0 | 1468 | 12.4 |
| 1961 | 17.3 | 1918 | 14.6 | 4804 | 0.0 | 2018 | 6.1 |
| 2635 | 8.0 | 2568 | 9.0 | 8327 | 0.0 | 2774 | 3.5 |
| 3540 | 0.0 | 3438 | 1.3 | 14432 | 0.0 | 3814 | 0.9 |
| 4756 | 0.0 | 4604 | 0.0 | 25013 | 0.0 | 5244 | 0.0 |
| 6390 | 0.0 | 6164 | 0.0 | 43352 | 0.0 | 7210 | 0.0 |
| 8585 | 0.0 | 8254 | 0.0 | 75137 | 0.0 | 9912 | 0.0 |
| 11534 | 0.0 | 11052 | 0.0 | 130228 | 0.0 | 13628 | 0.0 |
| 15497 | 0.0 | 14798 | 0.0 | 225710 | 0.0 | 18736 | 0.0 |
| 20820 | 0.0 | 19814 | 0.0 | 391198 | 0.0 | 25760 | 0.0 |
| Average Particle Diameter (nm) | 1051.4 | Average Particle Diameter (nm) | 1032.5 | Average Particle Diameter (nm) | 817.8 | Average Particle Diameter (nm) | 979.1 |
| Remarks | | Comparative Example | | Remarks | | Comparative Example | |

TABLE 6

| Sample No. | I-11 | Sample No. | I-12 |
|---|---|---|---|
| Nanoparticles (g) | 1.8 | Nanoparticles (g) | 2.0 |
| Trehalose (g) | 0.2 | Trehalose (g) | 0.0 |
| Dry Average Particle Diameter (μm) | 1.98 | Dry Average Particle Diameter (μm) | 1.80 |
| Specific Gravity | 1.31 | Specific Gravity | 1.34 |
| Aerodynamic Particle Diameter (μm) | 2.27 | Aerodynamic Particle Diameter (μm) | 2.08 |

| Wet Particle Diameter Distribution (immediately after) | | Wet Particle Diameter Distribution (10 minutes after) | | Wet Particle Diameter Distribution (immediately after) | | Wet Particle Diameter Distribution (10 minutes after) | |
|---|---|---|---|---|---|---|---|
| Particle Diameter (nm) | Volume (%) | Particle Diameter (nm) | Volume (%) | Particle Diameter (nm) | Volume (%) | Particle Diameter (nm) | Volume (%) |
| 17 | 0.0 | 16 | 0.0 | 6 | 0.0 | 6 | 0.0 |
| 23 | 0.0 | 22 | 0.0 | 9 | 0.0 | 9 | 0.0 |
| 32 | 0.0 | 30 | 0.0 | 14 | 0.0 | 14 | 0.0 |
| 44 | 0.0 | 42 | 0.0 | 21 | 0.0 | 22 | 0.0 |
| 60 | 0.0 | 57 | 0.0 | 31 | 0.0 | 34 | 0.0 |
| 82 | 0.0 | 79 | 0.0 | 47 | 0.0 | 52 | 0.0 |
| 113 | 0.0 | 108 | 0.0 | 70 | 0.0 | 79 | 0.0 |
| 156 | 0.0 | 149 | 0.1 | 105 | 0.0 | 122 | 0.1 |
| 215 | 0.3 | 205 | 0.4 | 158 | 0.0 | 187 | 0.3 |
| 295 | 6.3 | 281 | 2.2 | 237 | 0.9 | 287 | 5.7 |
| 406 | 13.1 | 386 | 4.7 | 355 | 8.6 | 441 | 12.2 |
| 559 | 14.5 | 531 | 14.9 | 532 | 31.8 | 677 | 16.8 |
| 769 | 17.5 | 730 | 29.2 | 797 | 41.4 | 1039 | 26.5 |
| 1058 | 14.2 | 1003 | 26.0 | 1194 | 17.3 | 1596 | 25.8 |
| 1455 | 4.7 | 1379 | 13.7 | 1789 | 0.0 | 2449 | 11.0 |
| 2002 | 4.2 | 1895 | 6.7 | 2680 | 0.0 | 3760 | 1.6 |
| 2754 | 10.4 | 2605 | 1.9 | 4016 | 0.0 | 5772 | 0.0 |
| 3790 | 10.4 | 3581 | 0.0 | 6018 | 0.0 | 8861 | 0.0 |
| 5214 | 3.9 | 4921 | 0.0 | 9019 | 0.0 | 13602 | 0.0 |
| 7173 | 0.3 | 6764 | 0.0 | 13514 | 0.0 | 20881 | 0.0 |
| 9869 | 0.0 | 9297 | 0.0 | 20251 | 0.0 | 32054 | 0.0 |
| 13577 | 0.0 | 12778 | 0.0 | 30346 | 0.0 | 49207 | 0.0 |
| 18680 | 0.0 | 17563 | 0.0 | 45472 | 0.0 | 75539 | 0.0 |
| 25700 | 0.0 | 24140 | 0.0 | 68140 | 0.0 | 115961 | 0.0 |
| Average Particle Diameter (nm) | 1496.1 | Average Particle Diameter (nm) | 943.8 | Average Particle Diameter (nm) | 738.0 | Average Particle Diameter (nm) | 1201.2 |
| Remarks | | Comparative Example | | Remarks | | Comparative Example | |

Each of the dry particle diameter distributions of nanocomposite particles of Sample Nos. I-1 to I-12 gave a single peak. It is revealed that the average particle diameter is about 2 μm without depending on the mass ratio of the nanoparticles to trehalose.

It is possible to evaluate redispersibility of nanoparticles by the measurement of wet particle diameter distribution of the nanocomposite particles obtained by the invention. It is possible to evaluate dispersion stability of the nanoparticles dispersion liquid by comparing results obtained by performing the measurement of the wet particle diameter distribution twice, namely, immediately after the addition of water and at 10 minutes after the addition of water.

It is apparent from Table 1 to Table 6 that each of the wet particle diameter distributions of the nanocomposite particles of Sample Nos. I-4 to I-8 gave a single peak, and the obtained nanoparticle dispersion liquid is of a monodisperse system. It is apparent that each of the wet particle diameter distributions of the nanocomposite particles of Sample Nos. I-5 to I-7 exhibits good redispersibility with a narrower distribution width. An average particle diameter is about 500 nm, which is substantially the same as that of the nanoparticles before the nanocomposite particle preparation. Also, since no major chance is observed with the particle diameter distribution in the measurement of 10 minutes after the water addition, it is proved that the nanoparticle dispersion liquid is stable.

In contrast, each of the wet particle diameter distributions of the nanocomposite particles of Sample Nos. I-1 to I-3 and I-9 to I-12 gave two peaks, from which it is apparent that the nanoparticles are not completely redispersed. Also, since no major change is observed with the wet particle diameter distribution in the measurement of 10 minutes after the water addition, it is proved that the nanoparticles are not completely redispersed.

As a summary of the foregoing results, it is proved that the nanocomposite particles of Sample Nos. I-4 to I-8 having the mass ratio of the nanoparticles to trehalose within the range of from 40:60 to 60:40 exhibit good redispersibility. Also, it is proved that the nanocomposite particles of Sample Nos. I-5 to I-7 having the mass ratio of the nanoparticles to trehalose within the range of from 45:55 to 55:45 exhibit better redispersibility.

Example 2

(1) Preparation of Nanoparticles

Rifampicin-containing PLGA nanoparticles were prepared iii the same manner as in Example 1 except for changing the supersonic wave irradiation conditions from "output: 10 W for 20 seconds" to "output: 20 W for 60 seconds".

The obtained PLGA nanoparticles were dispersed in distilled water, and, by a measurement of a particle diameter distribution using the wet particle diameter measurement device (ZETA SIZER HSA3000 manufactured by MALVERN), a particle diameter distribution having an average particle diameter of about 800 nm and a single peak were shown.

(2) Preparation and Measurements of Wet and Dry Particle Diameter Distributions of Nanocomposite Particles Nanocomposite particles were prepared in the same manner as in Example 1 except for using the nanoparticles (average particle diameter: about 800 nm) obtained as described above, and a dry particle diameter distribution and a wet particle diameter distribution were measured. Results are shown in Table 7.

TABLE 7

|  | Sample No. | | | | | |
|---|---|---|---|---|---|---|
|  | II-1 | | II-2 | | II-3 | |
|  | Nanoparticles (g) | | | | | |
|  | 0.9 | | 1.0 | | 1.1 | |
|  | Trehalose (g) | | | | | |
|  | 1.1 | | 1.0 | | 0.9 | |
|  | Dry Average Particle Diameter (μm) | | | | | |
|  | 1.78 | | 1.8 | | 1.57 | |
|  | Specific Gravity | | | | | |
|  | 1.46 | | 1.45 | | 1.44 | |
|  | Aerodynamic Particle Diameter (μm) | | | | | |
|  | 2.15 | | 2.16 | | 1.88 | |
|  | Particle Diameter (nm) | Volume (%) | Particle Diameter (nm) | Volume (%) | Particle Diameter (nm) | Volume (%) |
| Wet Particle Diameter Distribution (immediately after) | 120 | 0.0 | 6 | 0.0 | 5 | 0.0 |
|  | 142 | 0.0 | 9 | 0.0 | 8 | 0.0 |
|  | 168 | 0.0 | 14 | 0.0 | 12 | 0.0 |
|  | 198 | 0.0 | 21 | 0.0 | 18 | 0.0 |
|  | 233 | 0.0 | 33 | 0.0 | 29 | 0.0 |
|  | 275 | 0.0 | 51 | 0.0 | 44 | 0.0 |
|  | 325 | 0.0 | 78 | 0.0 | 69 | 0.0 |
|  | 383 | 0.0 | 120 | 0.0 | 107 | 0.0 |
|  | 452 | 0.4 | 184 | 0.0 | 167 | 0.0 |
|  | 533 | 2.5 | 283 | 2.7 | 260 | 2.4 |
|  | 629 | 24.5 | 436 | 9.3 | 404 | 10.7 |
|  | 742 | 44.8 | 672 | 28.9 | 628 | 30.8 |
|  | 875 | 24.5 | 1034 | 40.7 | 978 | 39.3 |
|  | 1033 | 2.7 | 1592 | 18.4 | 1521 | 16.7 |
|  | 1218 | 0.5 | 2451 | 0.0 | 2367 | 0.0 |
|  | 1437 | 0.0 | 3773 | 0.0 | 3682 | 0.0 |
|  | 1696 | 0.0 | 5809 | 0.0 | 5729 | 0.0 |
|  | 2001 | 0.0 | 8943 | 0.0 | 8914 | 0.0 |
|  | 2361 | 0.0 | 13767 | 0.0 | 13870 | 0.0 |
|  | 2785 | 0.0 | 21195 | 0.0 | 21580 | 0.0 |
|  | 3286 | 0.0 | 32630 | 0.0 | 33575 | 0.0 |
|  | 3877 | 0.0 | 50234 | 0.0 | 52240 | 0.0 |
|  | 4574 | 0.0 | 77336 | 0.0 | 81279 | 0.0 |
|  | 5396 | 0.0 | 119060 | 0.0 | 126461 | 0.0 |
| Average Particle Diameter (nm) | 749.9 | | 956.2 | | 881.3 | |
| Remarks | Example | | Example | | Example | |

From the measurement result of the wet particle diameter distribution, it is revealed that good redispersibility is exhibited when the mass ratio of the nanoparticles to trehalose is within the range of from 45:55 to 55:45 in the case where the nanocomposite particles were prepared by using the nanoparticles having the average particle diameter of about 800 nm.

Example 3

(1) Preparation of Nanoparticles

Rifampicin-containing PLGA nanoparticles were prepared in the same manner as in Example 1 except for changing the supersonic wave irradiation time from "20 seconds" to "5 minutes" and changing the centrifugation conditions from "10000 rpm for 10 minutes" to "35000 rpm for 15 minutes".

The obtained PLGA nanoparticles were dispersed in distilled water, and, by a measurement of a particle diameter distribution using the wet particle diameter measurement device (ZETA SIZER HSA3000 manufactured by MALVERN), a particle diameter distribution having an average particle diameter of about 250 nm and a single peak was shown.

(2) Preparation and Measurements of Dry Particle Diameter and Wet Particle Diameter Distribution of Nanocomposite Particles Nanocomposite particles were prepared in the same manner as in Example 1 except for using the nanoparticles (average particle diameter: about 250 nm) obtained as described above, and a dry average particle diameter and a wet particle diameter distribution were measured. Results are shown in Table 8.

TABLE 8

| | Sample No. | | |
|---|---|---|---|
| | III-1 | III-2 | III-3 |
| Nanoparticles (g) | 0.9 | 1.0 | 1.1 |
| Trehalose (g) | 1.1 | 1.0 | 0.9 |
| Dry Average Particle Diameter (μm) | 2.08 | 2.16 | 2.22 |
| Specific Gravity | 1.48 | 1.43 | 1.39 |
| Aerodynamic Particle Diameter (μm) | 2.53 | 2.58 | 2.61 |

| | III-1 | | III-2 | | III-3 | |
|---|---|---|---|---|---|---|
| | Particle Diameter (nm) | Volume (%) | Particle Diameter (nm) | Volume (%) | Particle Diameter (nm) | Volume (%) |
| Wet Particle Diameter Distribution (immediately after) | 9 | 0.0 | 9 | 0.0 | 14 | 0.0 |
| | 12 | 0.0 | 12 | 0.0 | 18 | 0.0 |
| | 17 | 0.0 | 16 | 0.0 | 23 | 0.0 |
| | 23 | 0.0 | 22 | 0.0 | 30 | 0.0 |
| | 31 | 0.0 | 30 | 0.0 | 39 | 0.0 |
| | 42 | 0.0 | 41 | 0.0 | 50 | 0.0 |
| | 57 | 0.0 | 55 | 0.0 | 65 | 0.0 |
| | 77 | 0.7 | 74 | 0.0 | 84 | 0.5 |
| | 105 | 3.1 | 101 | 0.0 | 109 | 2.5 |
| | 143 | 6.5 | 136 | 10.2 | 142 | 5.7 |
| | 194 | 9.7 | 184 | 32.8 | 183 | 8.7 |
| | 264 | 17.4 | 249 | 37.4 | 237 | 11.2 |
| | 358 | 28.7 | 337 | 17.2 | 307 | 23.6 |
| | 487 | 25.2 | 456 | 2.4 | 398 | 31.8 |
| | 662 | 8.6 | 617 | 0.0 | 515 | 15.3 |
| | 899 | 0.2 | 835 | 0.0 | 666 | 0.8 |
| | 1222 | 0.0 | 1129 | 0.0 | 863 | 0.0 |
| | 1662 | 0.0 | 1527 | 0.0 | 1117 | 0.0 |
| | 2258 | 0.0 | 2066 | 0.0 | 1446 | 0.0 |
| | 3070 | 0.0 | 2794 | 0.0 | 1872 | 0.0 |
| | 4172 | 0.0 | 3780 | 0.0 | 2424 | 0.0 |
| | 5671 | 0.0 | 5114 | 0.0 | 3138 | 0.0 |
| | 7708 | 0.0 | 6918 | 0.0 | 4063 | 0.0 |
| | 10476 | 0.0 | 9358 | 0.0 | 5260 | 0.0 |
| Average Particle Diameter (nm) | 361.9 | | 236.4 | | 336.7 | |
| Remarks | Example | | Example | | Example | |

From the measurement results of the wet particle diameter distribution, it is revealed that good redispersibility is exhibited when the mass ratio of the nanoparticles to trehalose is within the range of from 45:55 to 55:45 in the case where the nanocomposite particles were prepared by using the nanoparticles having the average particle diameter of about 250 nm.

As a summary of the foregoing results, it is proved that the redispersibility in water of the nanocomposite particles of the invention is irrelevant to the average particle diameter of the contained nanoparticles, and the good redispersibility is exhibited when the mass ratio of the nanoparticles to disaccharide is within the range of from 45:55 to 55:45 as depending on the mass ratio.

Example 4

1.0 g of PLGA nanoparticles (average particle diameter: about 500 nm) prepared in the same manner as in Example 1-(1) were redispersed in 100 ml of distilled water, and 1.0 g of trehalose was dissolved in the dispersion liquid to prepare a sample dispersion liquid. Nanocomposite particles were prepared in the same manner as in Example 1 except for performing the spray drying by using the thus-obtained sample dispersion liquid and varying the inlet temperature within the range of 60° C. to 120° C.

A dry particle diameter distribution and a wet particle diameter distribution were measured in the same manner as in Example 1. Results are shown in Table 9 and Table 10.

TABLE 9

| | Sample No. | | | | | | | |
|---|---|---|---|---|---|---|---|---|
| | IV-1 | | IV-2 | | IV-3 | | IV-4 | |
| | Nano-particles (g) | | | | | | | |
| | 1.0 | | 1.0 | | 1.0 | | 1.0 | |
| | Trehalose (g) | | | | | | | |
| | 1.0 | | 1.0 | | 1.0 | | 1.0 | |
| | Inlet Temperature (° C.) | | | | | | | |
| | 60 | | 70 | | 80 | | 90 | |
| | Dry Average Particle Diameter (μm) | | | | | | | |
| | 6.15 | | 6.33 | | 3.49 | | 2.46 | |
| | Particle Diameter (nm) | Volume (%) | Particle Diameter (nm) | Volume (%) | Particle Diameter (nm) | Volume (%) | Particle Diameter (nm) | Volume (%) |
| Wet Particle Diameter Distribution (immediately after) | 45 | 0.0 | 115 | 0.0 | 135 | 0.0 | 80 | 0.0 |
| | 54 | 0.0 | 128 | 0.0 | 148 | 0.0 | 93 | 0.0 |
| | 65 | 0.0 | 142 | 0.0 | 163 | 0.0 | 107 | 0.0 |
| | 79 | 0.0 | 157 | 0.0 | 179 | 0.0 | 124 | 0.0 |
| | 95 | 0.0 | 174 | 0.0 | 197 | 0.0 | 143 | 0.0 |
| | 114 | 0.0 | 193 | 0.0 | 217 | 0.0 | 165 | 0.0 |
| | 138 | 0.0 | 214 | 0.0 | 238 | 0.0 | 191 | 0.0 |
| | 166 | 0.2 | 237 | 0.0 | 262 | 0.0 | 220 | 0.2 |
| | 200 | 0.5 | 263 | 0.6 | 288 | 0.3 | 254 | 0.9 |
| | 242 | 1.2 | 292 | 2.6 | 317 | 1.8 | 294 | 2.5 |
| | 291 | 2.9 | 324 | 7.1 | 348 | 7.0 | 339 | 8.9 |
| | 351 | 21.2 | 359 | 17.1 | 383 | 25.9 | 392 | 26.9 |
| | 424 | 38.5 | 398 | 31.4 | 421 | 39.6 | 453 | 35.4 |
| | 511 | 22.0 | 441 | 30.2 | 463 | 22.4 | 523 | 18.0 |
| | 616 | 5.7 | 489 | 10.9 | 509 | 3.1 | 605 | 4.0 |
| | 743 | 5.4 | 542 | 0.0 | 560 | 0.0 | 699 | 2.4 |
| | 896 | 2.3 | 601 | 0.0 | 615 | 0.0 | 807 | 0.8 |
| | 1081 | 0.0 | 666 | 0.0 | 676 | 0.0 | 932 | 0.0 |
| | 1303 | 0.0 | 738 | 0.0 | 744 | 0.0 | 1077 | 0.0 |
| | 1572 | 0.0 | 818 | 0.0 | 818 | 0.0 | 1244 | 0.0 |
| | 1895 | 0.0 | 907 | 0.0 | 899 | 0.0 | 1437 | 0.0 |
| | 2286 | 0.0 | 1006 | 0.0 | 988 | 0.0 | 1660 | 0.0 |
| | 2756 | 0.0 | 1115 | 0.0 | 1087 | 0.0 | 1918 | 0.0 |
| | 3324 | 0.0 | 1236 | 0.0 | 1195 | 0.0 | 2216 | 0.0 |
| Average Particle Diameter (nm) | 458.4 | | 404.7 | | 416.3 | | 447.7 | |
| Remarks | Example | | Example | | Example | | Example | |

TABLE 10

| | Sample No. | | |
|---|---|---|---|
| | IV-5 | IV-6 | IV-7 |
| Nanoparticles (g) | 1.0 | 1.0 | 1.0 |
| Trehalose (g) | 1.0 | 1.0 | 1.0 |
| Inlet Temperature (°C.) | 100 | 110 | 120 |
| Dry Average Particle Diameter (μm) | 2.23 | 2.38 | 2.65 |

| | Particle Diameter (nm) | Volume (%) | Particle Diameter (nm) | Volume (%) | Particle Diameter (nm) | Volume (%) |
|---|---|---|---|---|---|---|
| Wet Particle Diameter Distribution (immediately after) | 86 | 0.0 | 5 | 0.0 | 15 | 0.0 |
| | 100 | 0.0 | 7 | 0.0 | 21 | 0.0 |
| | 117 | 0.0 | 11 | 0.0 | 30 | 0.0 |
| | 136 | 0.0 | 17 | 0.0 | 42 | 0.0 |
| | 159 | 0.0 | 27 | 0.0 | 58 | 0.0 |
| | 185 | 0.0 | 49 | 0.0 | 82 | 0.0 |
| | 215 | 0.0 | 65 | 0.0 | 116 | 0.0 |
| | 250 | 0.3 | 102 | 0.0 | 163 | 0.0 |
| | 291 | 1.3 | 158 | 0.3 | 230 | 0.3 |
| | 339 | 7.0 | 246 | 18.0 | 324 | 9.2 |
| | 395 | 21.3 | 382 | 40.8 | 456 | 20.0 |
| | 460 | 27.1 | 594 | 29.6 | 643 | 14.7 |
| | 536 | 15.0 | 923 | 7.8 | 905 | 4.9 |
| | 624 | 10.0 | 1435 | 2.0 | 1275 | 1.2 |
| | 727 | 12.3 | 2230 | 0.7 | 1796 | 2.0 |
| | 846 | 5.5 | 3467 | 0.0 | 2530 | 6.1 |
| | 985 | 0.1 | 5391 | 0.0 | 3564 | 14.4 |
| | 1147 | 0.0 | 8381 | 0.0 | 5020 | 18.8 |
| | 1336 | 0.0 | 13029 | 0.0 | 7071 | 8.4 |
| | 1556 | 0.0 | 20257 | 0.1 | 9959 | 0.0 |
| | 1811 | 0.0 | 31493 | 0.3 | 14028 | 0.0 |
| | 2109 | 0.0 | 48961 | 0.3 | 19759 | 0.0 |
| | 2456 | 0.0 | 76118 | 0.1 | 27831 | 0.0 |
| | 2860 | 0.0 | 118340 | 0.0 | 39200 | 0.0 |
| Average Particle Diameter (nm) | 516.8 | | 830.1 | | 2517.1 | |
| Remarks | Example | | Example | | Example | |

From Table 9 and Table 10, it is apparent that the dry average particle diameter increases with a reduction in inlet temperature. Also, it is revealed that it is possible to obtain the nanocomposite particles having good redispersibility by maintaining the inlet temperature within the range of from 60° C. to 100° C. in the preparation. In the case where trehalose was used as disaccharide, alteration of trehalose is prevented by maintaining the inlet temperature to 100° C. or less, thereby making it possible to impart the good redispersibility of the nanocomposite particles.

Example 5

Nanocomposite particles were prepared in the same manner as in Example 4 except for using lactose in place of trehalose, and a dry particle diameter distribution and a wet particle diameter distribution were measured. Results are shown in Table 11 and Table 12.

TABLE 11

| | Sample No. | | | | | | | |
|---|---|---|---|---|---|---|---|---|
| | V-1 | | V-2 | | V-3 | | V-4 | |
| | Nano-particles (g) | | | | | | | |
| | 1.0 | | 1.0 | | 1.0 | | 1.0 | |
| | Lactose (g) | | | | | | | |
| | 1.0 | | 1.0 | | 1.0 | | 1.0 | |
| | Inlet Temperature (° C.) | | | | | | | |
| | 60 | | 70 | | 80 | | 90 | |
| | Dry Average Particle Diameter (μm) | | | | | | | |
| | 5.69 | | 2.37 | | 2.37 | | 1.88 | |
| | Particle Diameter (nm) | Volume (%) | Particle Diameter (nm) | Volume (%) | Particle Diameter (nm) | Volume (%) | Particle Diameter (nm) | Volume (%) |
| Wet Particle Diameter Distribution (immediately after) | 43 | 0.0 | 53 | 0.0 | 52 | 0.0 | 51 | 0.0 |
| | 52 | 0.0 | 63 | 0.0 | 62 | 0.0 | 61 | 0.0 |
| | 62 | 0.0 | 74 | 0.0 | 74 | 0.0 | 72 | 0.0 |
| | 75 | 0.0 | 88 | 0.0 | 87 | 0.0 | 86 | 0.0 |
| | 90 | 0.0 | 104 | 0.0 | 103 | 0.0 | 103 | 0.0 |
| | 108 | 0.0 | 123 | 0.0 | 123 | 0.0 | 122 | 0.0 |
| | 130 | 0.1 | 146 | 0.0 | 146 | 0.0 | 146 | 0.0 |
| | 156 | 0.5 | 173 | 0.1 | 173 | 0.0 | 174 | 0.0 |
| | 188 | 1.2 | 205 | 0.6 | 205 | 0.0 | 207 | 0.0 |
| | 226 | 2.3 | 243 | 1.9 | 243 | 0.9 | 247 | 0.7 |
| | 273 | 4.3 | 287 | 4.8 | 288 | 10.0 | 294 | 4.6 |
| | 328 | 14.2 | 341 | 20.0 | 342 | 33.1 | 350 | 28.3 |
| | 395 | 28.7 | 403 | 36.8 | 406 | 40.0 | 417 | 45.4 |
| | 475 | 26.7 | 478 | 27.2 | 482 | 15.9 | 498 | 21.0 |
| | 571 | 13.2 | 566 | 7.8 | 571 | 0.0 | 593 | 0.0 |
| | 687 | 6.2 | 671 | 0.8 | 678 | 0.0 | 707 | 0.0 |
| | 827 | 2.5 | 795 | 0.0 | 804 | 0.0 | 843 | 0.0 |
| | 995 | 0.1 | 941 | 0.0 | 954 | 0.0 | 1004 | 0.0 |
| | 1198 | 0.0 | 1115 | 0.0 | 1132 | 0.0 | 1197 | 0.0 |
| | 1441 | 0.0 | 1321 | 0.0 | 1343 | 0.0 | 1427 | 0.0 |
| | 1734 | 0.0 | 1565 | 0.0 | 1593 | 0.0 | 1701 | 0.0 |
| | 2087 | 0.0 | 1854 | 0.0 | 1890 | 0.0 | 2027 | 0.0 |
| | 2511 | 0.0 | 2196 | 0.0 | 2242 | 0.0 | 2416 | 0.0 |
| | 3022 | 0.0 | 2602 | 0.0 | 2660 | 0.0 | 2880 | 0.0 |
| Average Particle Diameter (nm) | 446.3 | | 415.8 | | 383.2 | | 408.3 | |
| Remarks | Example | | Example | | Example | | Example | |

TABLE 12

| | Sample No. | | | | | |
|---|---|---|---|---|---|---|
| | V-5 | | V-6 | | V-7 | |
| | Nanoparticles (g) | | | | | |
| | 1.0 | | 1.0 | | 1.0 | |
| | Lactose (g) | | | | | |
| | 1.0 | | 1.0 | | 1.0 | |
| | Inlet Temperature (° C.) | | | | | |
| | 100 | | 110 | | 120 | |
| | Dry Average Particle Diameter (μm) | | | | | |
| | 2.29 | | 2.58 | | 2.58 | |
| | Particle Diameter (nm) | Volume (%) | Particle Diameter (nm) | Volume (%) | Particle Diameter (nm) | Volume (%) |
| Wet Particle Diameter Distribution (immediately after) | 18 | 0.0 | 14 | 0.0 | 10 | 0.0 |
| | 24 | 0.0 | 19 | 0.0 | 15 | 0.0 |
| | 33 | 0.0 | 97 | 0.0 | 21 | 0.0 |
| | 45 | 0.0 | 37 | 0.0 | 31 | 0.0 |
| | 61 | 0.0 | 51 | 0.0 | 46 | 0.0 |
| | 82 | 0.0 | 70 | 0.0 | 68 | 0.0 |

TABLE 12-continued

| | Sample No. | | |
|---|---|---|---|
| | V-5 | V-6 | V-7 |
| Nanoparticles (g) | 1.0 | 1.0 | 1.0 |
| Lactose (g) | 1.0 | 1.0 | 1.0 |
| Inlet Temperature (° C.) | 100 | 110 | 120 |
| Dry Average Particle Diameter (μm) | 2.29 | 2.58 | 2.58 |
| Particle Diameter (nm) | Volume (%) | Particle Diameter (nm) | Volume (%) | Particle Diameter (nm) | Volume (%) |
|---|---|---|---|---|---|
| 111 | 0.0 | 96 | 0.0 | 99 | 0.0 |
| 151 | 0.1 | 132 | 0.0 | 146 | 0.1 |
| 205 | 0.7 | 182 | 0.3 | 214 | 0.4 |
| 278 | 4.4 | 251 | 5.0 | 314 | 3.9 |
| 377 | 10.6 | 346 | 16.6 | 461 | 9.5 |
| 511 | 20.3 | 476 | 19.7 | 677 | 13.3 |
| 693 | 27.8 | 656 | 9.4 | 994 | 14.6 |
| 940 | 21.6 | 903 | 14.4 | 1460 | 11.5 |
| 1275 | 10.9 | 1244 | 23.6 | 2145 | 16.1 |
| 1729 | 3.5 | 1713 | 11.0 | 3150 | 21.2 |
| 2345 | 0.0 | 2359 | 0.0 | 4626 | 9.4 |
| 3180 | 0.0 | 3249 | 0.0 | 6793 | 0.0 |
| 4313 | 0.0 | 4474 | 0.0 | 9977 | 0.0 |
| 5849 | 0.0 | 6161 | 0.0 | 14652 | 0.0 |
| 7932 | 0.0 | 8485 | 0.0 | 21518 | 0.0 |
| 10757 | 0.0 | 11685 | 0.0 | 31602 | 0.0 |
| 14588 | 0.0 | 16091 | 0.0 | 46411 | 0.0 |
| 19784 | 0.0 | 22160 | 0.0 | 68160 | 0.0 |
| Average Particle Diameter (nm) | 752.8 | | 838.0 | | 1908.1 |
| Remarks | Example | | Example | | Example |

From Table 11 and Table 12, it is apparent that the dry average particle diameter increases with a reduction in inlet temperature. Also, it is revealed that it is possible to obtain the nanocomposite particles having good redispersibility by maintaining the inlet temperature within the range of from 60° C. to 90° C. in the preparation. In the case where lactose was used as disaccharide, alteration of lactose is prevented by maintaining the inlet temperature to 90° C. or less, thereby making it possible to impart the good redispersibility of the nanocomposite particles.

As a summary of the foregoing results, it is possible to prepare the nanocomposite particles exhibiting the good redispersibility when the inlet temperature of the spray drying machine in the spray drying is within the range of from 60° C. to 100° C.

Also, it is revealed that it is possible to achieve an aerodynamic particle diameter distribution suitable for delivering the nanocomposite particles of the invention to the alveoli when the inlet temperature is 70° C. or more. Therefore, it is proved that, by maintaining the inlet temperature of the spray drying machine within the range of from 70° C. to 100° C. it is possible to prepare the nanocomposite particles having good characteristics as a pulmonary administration preparation in terms of the redispersibility and the aerodynamic particle diameter distribution. Further, it is proved that better characteristics are obtained when the inlet temperature of the spray drying machine is within the range of from 80° C. to 90° C.

Comparative Example 1

1.0 g of PLGA nanoparticles (average particle diameter: about 250 nm) prepared in the same manner as in Example 3-(1) was redispersed in 100 ml of distilled water, and 1.0 g of mannitol was dissolved in the dispersion liquid to prepare a sample dispersion liquid. Nanocomposite particles were prepared in the same manner as in Example 1 except for using the thus-obtained sample dispersion liquid, and a dry average particle diameter and a wet particle diameter distribution were measured, Results are shown in Table 13. Note that the measurement results of Sample No. III-2 are also shown in Table 13 for the purpose of comparison.

TABLE 13

| Sample No. | | VI | | Sample No. | | III-2 | |
|---|---|---|---|---|---|---|---|
| Nanoparticles (g) | | 1.0 | | Nanoparticles (g) | | 1.0 | |
| Mannitol (g) | | 1.0 | | Trehalose (g) | | 1.0 | |
| Dry Average Particle Diameter (μm) | | 2.47 | | Dry Average Particle Diameter (μm) | | 2.16 | |
| Wet Particle Diameter Distribution (immediately after) | | Wet Particle Diameter Distribution (10 minutes after) | | Wet Particle Diameter Distribution (immediately after) | | Wet Particle Diameter Distribution (10 minutes after) | |
| Particle Diameter (nm) | Volume (%) | Particle Diameter (nm) | Volume (%) | Particle Diameter (nm) | Volume (%) | Particle Diameter (nm) | Volume (%) |
| 3 | 0.0 | 3 | 0 | 9 | 0.0 | 14 | 0 |
| 5 | 0.0 | 5 | 0 | 12 | 0.0 | 18 | 0 |
| 7 | 0.0 | 7 | 0 | 16 | 0.0 | 23 | 0 |
| 11 | 0.0 | 11 | 0 | 22 | 0.0 | 30 | 0 |
| 16 | 0.0 | 16 | 0 | 30 | 0.0 | 39 | 0 |
| 25 | 0.0 | 24 | 0 | 41 | 0.0 | 50 | 0 |
| 37 | 0.0 | 37 | 0 | 55 | 0.0 | 65 | 0 |
| 55 | 0.0 | 55 | 0 | 74 | 0.0 | 85 | 0 |
| 83 | 1.2 | 82 | 1.5 | 101 | 0.0 | 110 | 1.4 |
| 124 | 8.3 | 123 | 7.5 | 136 | 10.2 | 142 | 7.4 |
| 186 | 14.8 | 185 | 13.5 | 184 | 32.8 | 185 | 17 |
| 279 | 9.5 | 277 | 10.4 | 249 | 37.4 | 239 | 23.7 |
| 419 | 1.8 | 415 | 2.9 | 337 | 17.2 | 310 | 25.4 |
| 629 | 2.7 | 623 | 1.4 | 456 | 2.4 | 402 | 18.9 |
| 944 | 18.7 | 934 | 17.4 | 617 | 0.0 | 522 | 6.2 |
| 1416 | 29.5 | 1401 | 30.7 | 835 | 0.0 | 676 | 0 |
| 2125 | 13.4 | 2102 | 14.7 | 1129 | 0.0 | 877 | 0 |
| 3188 | 0.0 | 3153 | 0 | 1527 | 0.0 | 1137 | 0 |
| 4784 | 0.0 | 4730 | 0 | 2066 | 0.0 | 1474 | 0 |
| 7178 | 0.0 | 7095 | 0 | 2974 | 0.0 | 1911 | 0 |
| 10770 | 0.0 | 10643 | 0 | 3780 | 0.0 | 2478 | 0 |
| 16159 | 0.0 | 15946 | 0 | 5114 | 0.0 | 3213 | 0 |
| 24246 | 0.0 | 23946 | 0 | 6918 | 0.0 | 4166 | 0 |
| 36380 | 0.0 | 35920 | 0 | 9358 | 0.0 | 5402 | 0 |
| Average Particle Diameter (nm) | 968.9 | Average Particle Diameter (nm) | 986.7 | Average Particle Diameter (nm) | 236.4 | Average Particle Diameter (nm) | 287.3 |
| Remarks | | Comparative Example | | Remarks | | Example | |

From Table 13, it is apparent that, in the case where mannitol which is a sugar alcohol was used in place of trehalose which is disaccharide, the wet average particle diameter gives two peaks, and the nanoparticles are not completely redispersed. Also, since no major change is observed with the wet particle diameter distribution in the measurement of 10 minutes after the water addition, it is proved that the nanoparticles remain not completely redispersed.

Example 6

Figure 1:
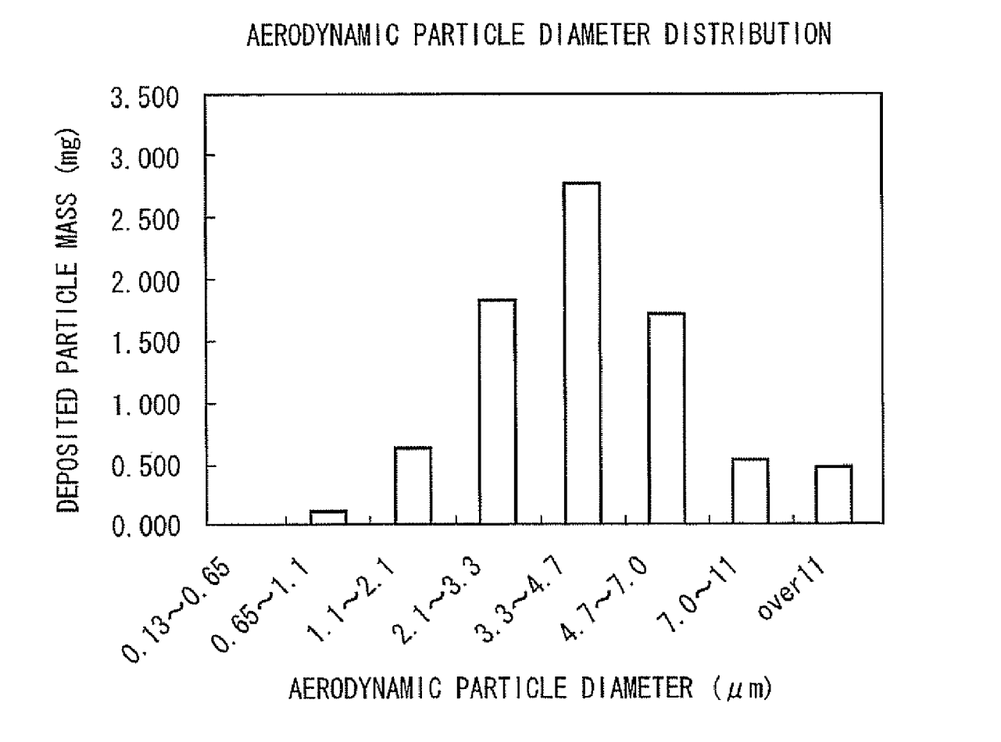

An aerodynamic particle diameter distribution of the nanocomposite particles of each of Sample Nos. (III-1) to (III-3) obtained by Example 3 was evaluated by using an Andersen type cascade impactor and employing the following procedure.

(1) The measurement sample was vacuum dried for two hours in a vacuum drier, and 30 mg of the measurement sample was weighed in a measurement capsule.

(2) By using the Andersen type cascade impactor (AN-200 manufactured by Tokyo Dylec Corp.) and a dry powder inhaler (DPI, Jethaler manufactured by Hitachi, Ltd.), suction was performed for 5 seconds at a flow rate of 28.3 l/min.

(3) A particle deposition amount on each of the stages was calculated by dissolving the deposited particles in chloroform and measuring absorbance (wavelength: 475 mm) of RFP in the chloroform.

(4) An in-capsule residual particle amount was calculated by measuring a mass of the capsule again, and a particle release amount was calculated from a difference with the charged amount.

(5) An FPF (Fine Particle Fraction)(%) which is a proportion of a total of particle masses deposited in the stages 3 to 7 (lower stages) to a total particle mass was calculated.

Table 14 shows particle release efficiency ED (%), deposited particle masses (mg) of stages 0 to 7, and FPF (%) of the samples. Also, the aerodynamic particle diameter distribution of Sample (III-2) is shown in FIG. 1.

TABLE 14

| | | Sample No. | | |
|---|---|---|---|---|
| | | III-1 | III-2 | III-3 |
| Nanoparticles (g) | | 0.9 | 1.0 | 1.1 |
| Trehalose (g) | | 1.1 | 1.0 | 0.9 |
| Charged Amount (mg) | | 30.2 | 30.3 | 30.2 |
| Particle Release Amount (mg) | | 27.6 | 29.0 | 28.4 |
| ED (%) | | 91.4 | 95.7 | 94.0 |
| Mass of Deposited Particles in Each of Stages (mg) | 0 | 0.60050 | 0.47062 | 0.36243 |
| | 1 | 0.44141 | 0.54229 | 0.45916 |
| | 2 | 1.38902 | 1.71840 | 4.79857 |
| | 3 | 3.03600 | 2.78857 | 1.58612 |
| | 4 | 2.95989 | 1.84334 | 2.52452 |
| | 5 | 1.04172 | 0.62610 | 0.93068 |
| | 6 | 0.16785 | 0.11715 | 0.15967 |
| | 7 | 0.00000 | 0.00000 | 0.00000 |
| FPF (%) | | 23.9 | 17.7 | 17.2 |

From Table 14, it is apparent that each of Samples (III-1) to (III-3) shows good particle release efficiency.

The FPF is a value suitably used for evaluating the degree of delivery to the alveoli, and the larger the FPF, the more excellent the delivery to the alveoli becomes. It is apparent that each of Samples (III-1) to (III-3) shows a good FPF. That is, it is apparent that Samples (III-1) to (III-3) have a large proportion of particles having an aerodynamic particle diameter of 0.13 to 4.7 µm that is suitable for delivery to alveoli and exhibit a favorable flying property.

Therefore, according to the nanocomposite particles of the invention, which include nanoparticles containing a drug to delivered and a biodegradable polymer, and a sugar material, and in which the sugar material is disaccharide, and the mass ratio of the nanoparticles to the disaccharide is within the range of from 40:60 to 60:40, it is possible to provide nanocomposite particles having good solubility in water and good redispersibility when brought into contact with water.

The invention claimed is:

1. Nanocomposite particles comprising a sugar material and nanoparticles including a drug to be delivered and a biodegradable polymer, wherein the sugar material is at least one disaccharide selected from the group consisting of sucrose, maltose, lactose, trehalose, and cellobiose; and a mass ratio of the nanoparticles to the disaccharide is within a range of from 45:55 to 55:45, wherein the nanocomposite particles have a dry average particle diameter ranging from 1.58 µm to 6.15 µm and the nanoparticles form a monodispersion having a diameter ranging from 250 nm to 900 nm when the nanocomposite particles are placed in distilled water.

2. The nanocomposite particles according to claim 1, wherein the biodegradable polymer is a biodegradable polymer comprising at least one selected from the group consisting of polylactic acid, polyglycolic acid, poly(lactic acid-glycolic acid), and polycyanoacrylate.

3. The nanocomposite particles according to claim 1, wherein the biodegradable polymer is a biodegradable polymer comprising poly(lactic acid-glycolic acid) and the disaccharide is lactose and/or trehalose.

4. The nanocomposite particles according to claim 1, wherein the nanocomposite particles are obtained by spray drying a solution comprising the nanoparticles and the disaccharide.

5. The nanocomposite particles according to claim 4, wherein an inlet temperature of a spray drying machine in the spray drying is within a range of from 60° C. to 100° C.

6. The nanocomposites particle according to claim 4, wherein an inlet temperature of the spray drying machine in the spray drying is within a range of from 60° C. to 90° C.

7. A production method for the nanocomposite particles according to claim 1, the method comprising spray drying a solution comprising nanoparticles comprising a drug to be delivered and disaccharide.

8. The production method for the nanocomposite particles according to claim 7, wherein an inlet temperature of a spray drying machine in the spray drying is within a range of from 60° C. to 100° C.

9. The production method for the nanocomposite particles according to claim 7, wherein an inlet temperature of the spray drying machine in the spray drying is within a range of from 60° C. to 90° C.

* * * * *